(12) United States Patent
Beckham et al.

(10) Patent No.: US 6,331,246 B1
(45) Date of Patent: Dec. 18, 2001

(54) WASTE FILTER AND MANIFOLD SYSTEM

(75) Inventors: Scott Beckham, Newport Beach; Dale Emis, Mission Viejo; Nilesh Patel, Laguna Niguel, all of CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/566,491

(22) Filed: May 8, 2000

(51) Int. Cl.$^7$ ..................................................... B01D 35/30
(52) U.S. Cl. ........................ 210/136; 137/606; 137/545; 210/339; 210/435
(58) Field of Search ..................... 210/136, 232, 210/240, 323.1, 335, 339, 346, 420, 456, 435, 541; 137/855, 606, 549, 550, 544; 604/83, 247

(56) References Cited

U.S. PATENT DOCUMENTS

Re. 24,255 * 12/1956 Lund .
110,136 * 12/1870 Hemenway .
493,378 * 3/1893 Gibson .
4,141,379 * 2/1979 Manske .
4,443,336 * 4/1984 Bennethum .
4,915,688 * 4/1990 Bischof .

\* cited by examiner

Primary Examiner—Joseph W. Drodge
Assistant Examiner—Terry K. Cecil
(74) Attorney, Agent, or Firm—G. Donald Weber, Jr.

(57) ABSTRACT

A filter system especially useful in the treatment of waste material, in particular liquid waste material which may include particulate matter therein. The filter system includes a series of filters of progressively finer porosity in order to selectively eliminate particulate (or semi-particulate) matters from a carrier material, typically but not exclusively, of a fluid or liquid nature. The filters are mounted within a housing which includes an outlet port and a plurality of inlet ports, wherein each inlet port includes a check valve.

20 Claims, 6 Drawing Sheets

WASTE FILTER AND MANIFOLD SYSTEM

BACKGROUND

1. Field of the Invention

This invention is directed to a filter system, in general, and, more particularly, to a filter system for removing solids or semi-solids from a fluid or liquid carrier.

2. Prior Art

There are many uses for filter systems and/or devices for removing certain types of materials from a carrier. One such application is the removal of solid or semi-solid detritus such as bone chips, flesh, blood clots or the like from the waste material generated by a medical procedure or operation. This removal process permits the liquid or fluid carrier to be treated separately from the other debris which is trapped by the filtration process. Of course, filtration processes are not limited to the medical field, per se, but can be used in areas such as clean rooms or other sterile environments.

SUMMARY OF THE INSTANT INVENTION

The invention relates to a filter system which is especially useful in the treatment of waste material, in particular liquid waste material which may include particulate matter therein. The filter system includes filtration means, for example, a series of filters of increasingly finer porosity in order to selectively eliminate particulate and/or or semi-particulate matter from a fluid or liquid carrier material passing through the filter system. The filters are mounted within a housing which includes one or more inlet ports and at least one outlet port so that multiple input sources can be accommodated, if so desired. The system includes appropriate check valve devices to establish unidirectional flow to prevent reverse flow of effluent therethrough. The filter materials are intended (but are not required) to be disposable. The housing may also be disposable, if preferred.

DESCRIPTION OF A PREFERRED EMBODIMENT

Figure 1:
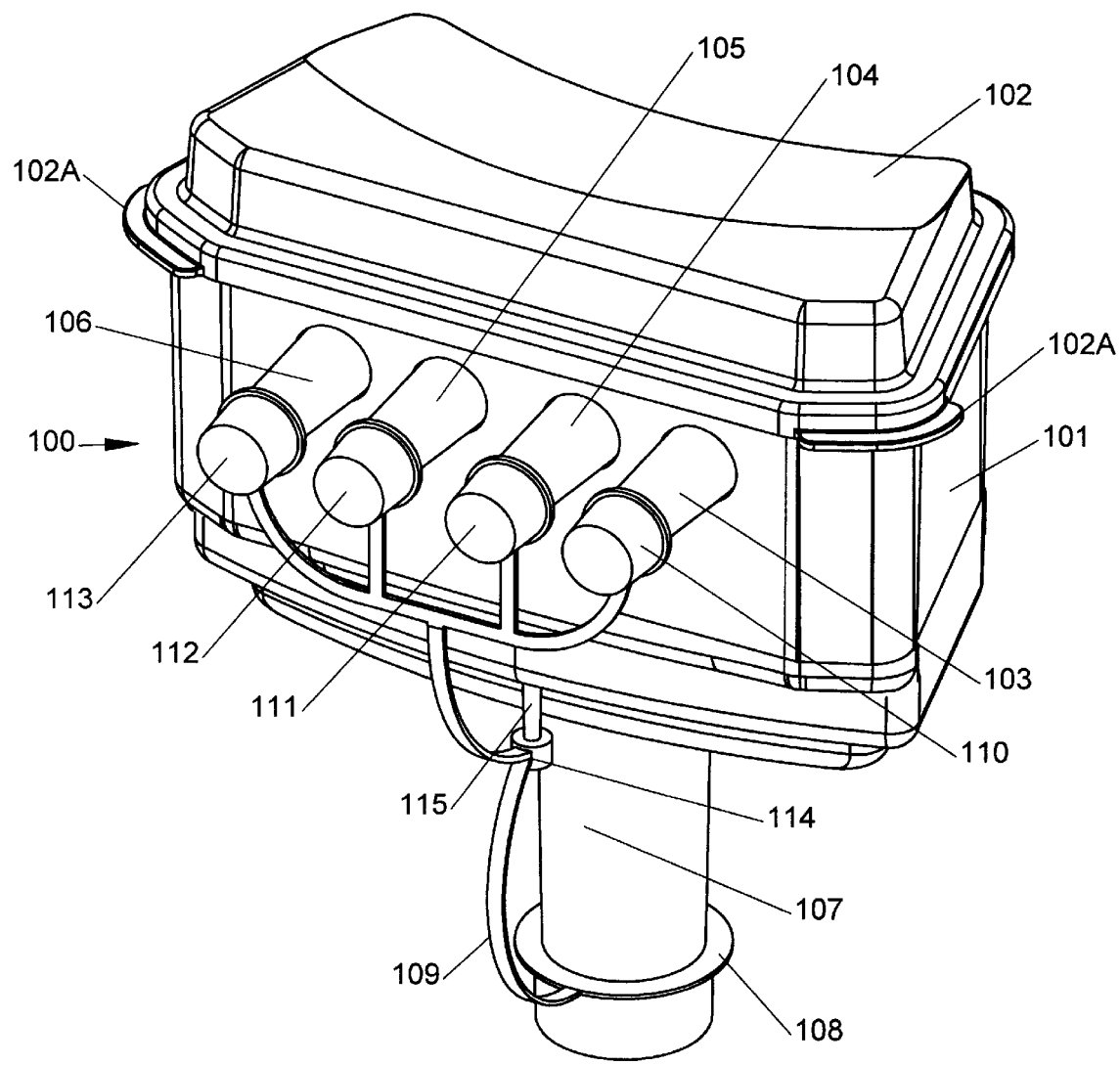
FIG. 1 is an oblique view of one embodiment of the housing for the filtration system of the instant invention.

Referring now to FIG. 1 there is shown an oblique, external view of a preferred embodiment of the housing for the filter manifold system 100 of the instant invention. The system 100 includes a generally hollow housing 101 and a removable lid 102. The lid 102 can include one or more ears 102A which are useful in removing the lid from the housing.

A plurality of inlet ports 103–106 are shown projecting outwardly from the front surface of housing 101. As will be noted infra, the inlet ports can be integrally formed with the housing. Alternatively, the inlet ports, the number of which is not a critical part of the invention, per se, can be formed as a separate assembly which is conveniently mounted at the housing 101 (see infra at FIG. 2). The inlet ports 103–106 are provided to be connected to a suitable source of material to be filtered by means of a suitable conduit. In a typical application, the conduit comprises conventional "plastic" tubing.

As shown in this embodiment, the outlet port 107 depends from the bottom of the housing 101 and is adapted to drain and conduct the filtered contents of the housing 101 to a suitable receiver. Again while not intended to be limitative of the invention, the outlet port is inserted into a conduit such as conventional tubing.

An optional feature of the manifold system 100 comprises the port caps 110–113 which fit snugly over the outer ends of the inlet ports 103–106, respectively. In this embodiment, the port caps 110–113 are attached together via a flexible cap leash 109. The configuration of the leash, typically a thin plastic strip, can vary as a function of design preference. In this embodiment, the leash includes a cap ring 108 which is adapted to encircle and engage the outlet port 107 for convenience. In addition, the leash 109 includes a leash grommet 114 which is adapted to engage a leash pin 115 which depends from the lower front portion of the housing 101. In this embodiment, the leash grommet and cap ring are formed as an integral unit.

In use, the port caps 110–113 are used to cover any of the inlet ports 103–106 which are not connected to an input source (not shown) as described supra, in order to maintain the integrity of the filtration system 100, in general, and to prevent leakage through the housing 101, in particular. The port caps can, of course, be individually provided (with or without individual leashes) and need not be connected by a common leash 109.

Figure 2:
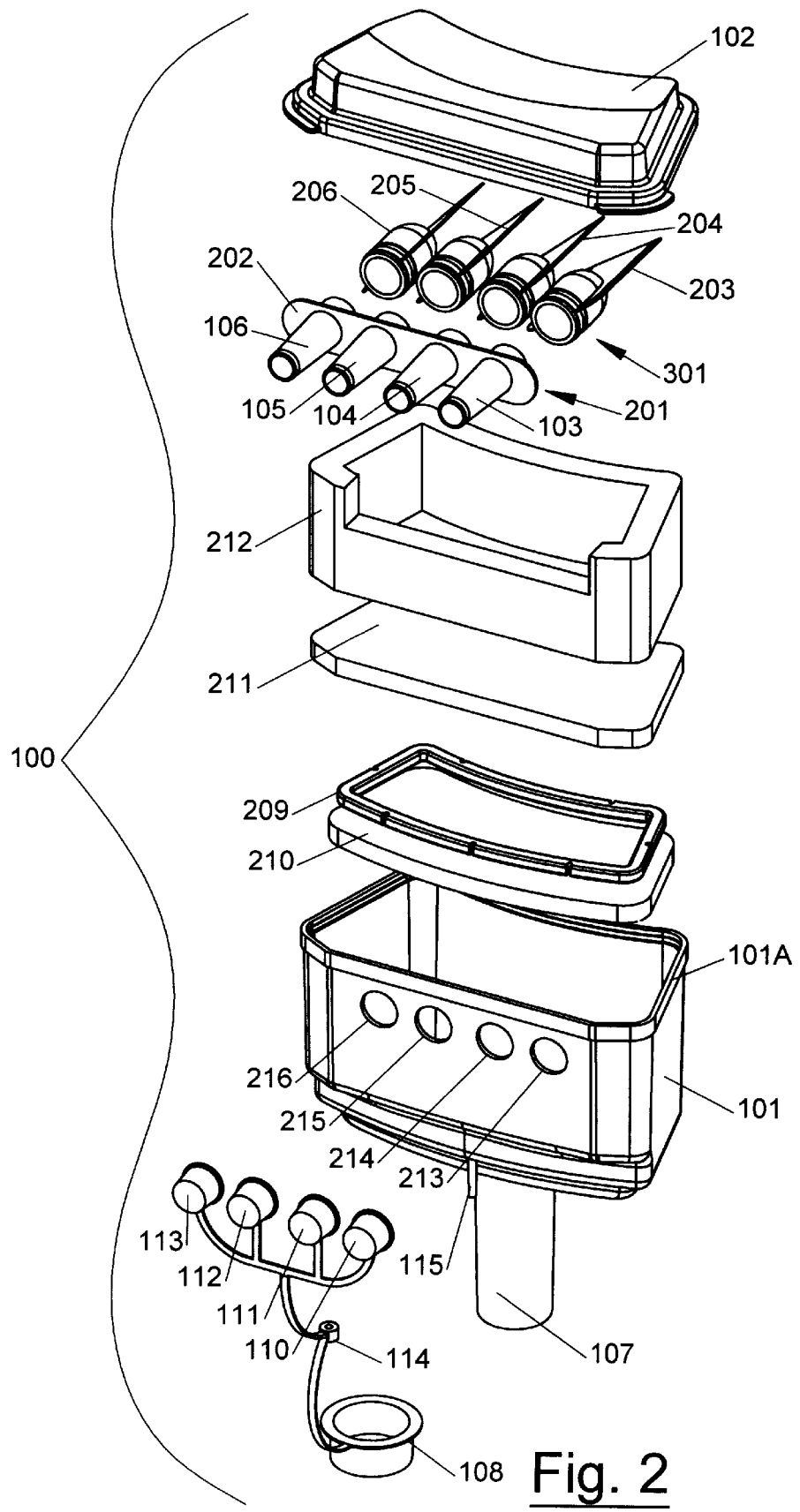
FIG. 2 is an exploded view of one embodiment of the filtration system of the instant invention.

Referring now to FIG. 2 there is shown an exploded view of the system 100. Typically, the lid 102 is formed of polyethylene and includes a peripheral groove (see infra at FIG. 3) which receives and snugly engages the upper edge 101A or lip of the housing 101. In this embodiment, the housing 101 is formed of ABS and is, generally, rectangular in configuration with a slightly arcuate rear surface (which is provided for mounting purposes in one typical application). The outlet port 107 depends from the bottom of the housing 101.

In this embodiment, a plurality of inlet port openings 213–216 are provided through the front surface of the housing 101. That is, as suggested supra, the inlet ports 103–106 can be formed on a common support base 202, and take the form of a separate assembly 201. In this case, the assembly 201 is placed inside the housing 101 with the proximal ends of the ports extending outwardly through the ports openings. The support base 202 is, typically, affixed to the inner surface of the housing in any suitable manner. Of course, in the embodiment wherein the inlet ports are formed as integral parts of the housing 101, per se, the separate openings 213–216 are unnecessary.

The port caps 110–113 and the related cap leash 109 (and components 108 and 114 thereof) are adapted to be mounted to the assembly as suggested in FIG. 1 whether the inlet ports are separate or integral with the housing 101. Again, the leash 109 (and the design thereof) is not a critical portion of the invention.

A plurality of check valves 203–206 are adapted to be attached to each of the inner ends of the inlet ports 103–106, respectively. Each of the check valves, described in greater detail infra, includes a connection portion, for example connector 301, (generally cylindrical in this embodiment) which is the proximal end of the check valve and is adapted to be snugly joined to the inner (distal) end of the respective inlet port and a flexible distal end which permits fluid flow through the check valve in one direction only as described infra relative to FIGS. 6, 7 and 8.

Mounted within the housing 101 is a filter element 210 which is the least porous filter elements in the preferred embodiment. Typically, filter element 210 is fabricated of reticulated polyurethane foam and is, in a preferred embodiment, about 0.3 inches thick. In this embodiment, element 210 has approximately 100 pores per linear inch although this parameter can vary in accordance with the application of the filter system.

Mounted within housing 101 immediately above filter element 210 is the filter support gasket 209 which is fabricated of ABS and, thus, provides a rather rigid gasket. Typically, gasket 209 conforms somewhat snugly to the inner perimeter of housing 101. The gasket 209 is, typically, affixed to the inner surface of the housing by any suitable method such as adhesives, bonding, frictional force fit, sonic welding or the like. Thus, the gasket 209 maintains the filter element 210 in position whereby the outlet port 107 remains open (i.e. unclogged by the filter components) and, as well, prevents leakage flow to outlet port 107 around the filter elements.

Mounted above filter element 210 is filter element 211 wherein element 211 is typically, more porous than filter element 210. In the preferred embodiment, filter element 211 contains about 30 pores per linear inch and is about 0.3 inches thick. Element 211 is, typically, fabricated of reticulated polyurethane foam and extends snugly to the internal surfaces of housing 101 to prohibit flow therearound. The filter element 211 tends to rest loosely upon support gasket 209 and the upper surface of filter element 209.

Also, mounted in the housing 101 is filter element 212 which is the most porous filter element in this embodiment. Typically, element 212 is fabricated of reticulated polyurethane foam and has about 5 pores per linear inch. It is noted that element 212 has a configuration which advantageously substantially surrounds the inner (distal) ends of the check valves 203–206. In this embodiment, the configuration of the element 212 is such that the wall thicknesses thereof are about 0.5 inch while the height of the back and sides is about 1.5 inches. This element has the effect of confining any effluent which passes through the check valves 203–206 so that the effluent material flow must pass through the filtration portion of system 100 in order to traverse from the inlet ports to the outlet port.

The filter element 212 may be fabricated in the "sofa" configuration as shown. Alternatively, the filter element can be fabricated from a flat sheet of material which is cut to shape and folded into the depicted shape.

It must be understood, of course, that the specific configurations and/or parameters of any of the filter elements are desirable but can be varied in accordance with the specific filtration process required. In fact, some or all of the filtration elements may be combined or eliminated as a single filter element, if so desired.

Figure 3:
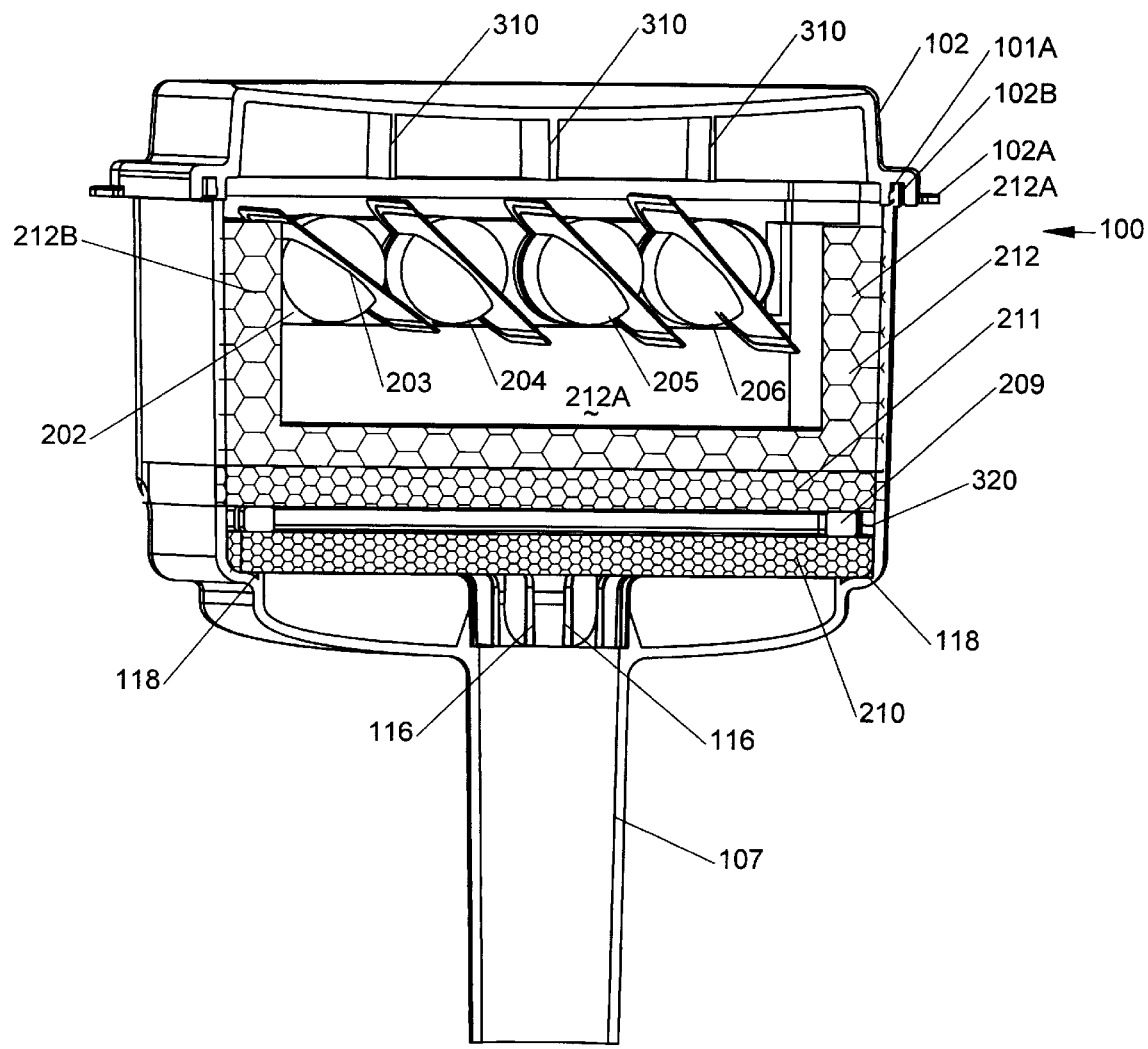
FIG. 3 is a partially broken away rear view of a preferred embodiment of the filtration system of the instant invention.

Referring now to FIG. 3, there is shown a partially broken away view of the system 100 taken through the rear of the housing 101. There is shown the interior of the front surface of the housing 101 with the distal end of check valves 203–206 extending inwardly. The outlet port 107 extends downwardly from the housing. Lid 102 includes the groove 102B which is secured to the edge 101A of housing 101. The ribs 310 provide support and rigidity to lid 102 and can be omitted in some designs.

As seen, filter element 210 is mounted adjacent to the bottom of the housing 101 and above the outlet port 107. A partial shading suggests the fine porosity of filter 210.

The support gasket 209 is disposed above filter element 210 and, as noted, secured to the housing 101. In one embodiment, upright pins 320 extend upwardly from the inner bottom surface of housing 101. The pins 320 extend through filter 210 and engage apertures in gasket 209 to secure the gasket and the filter 210 to the housing 101. This arrangement maintains filter element 210 in position and affords a support for the other filter elements. The pins 320, if utilized, can be treated to assist in securing the gasket 209 to the housing 101.

Filter element 211 rests upon gasket 209 and, to some extent, upon filter element 210. The partial shading of filter element 211 suggests a more porous structure than filter element 210.

Filter element 212 is also provided in housing 101 and adjacent to the check valves 203–206. As shown, filter element 212 rests upon filter element 211 and substantially surrounds the inner (distal) ends of the check valves. That is, the filter element 212 includes side walls 212A and 212B which extend upwardly along the side walls of the housing 101 into close proximity to the inner surface of lid 102. Thus, effluent from the check valves is contained within filter element 212 to insure filtration of all of the effluent. The partial shading of filter element 212 suggests a structure which is more porous than filter element 211.

In FIG. 3, the support base 202 for the inlet ports 103–106 is shown although this support base may be eliminated as described supra.

Figure 4:
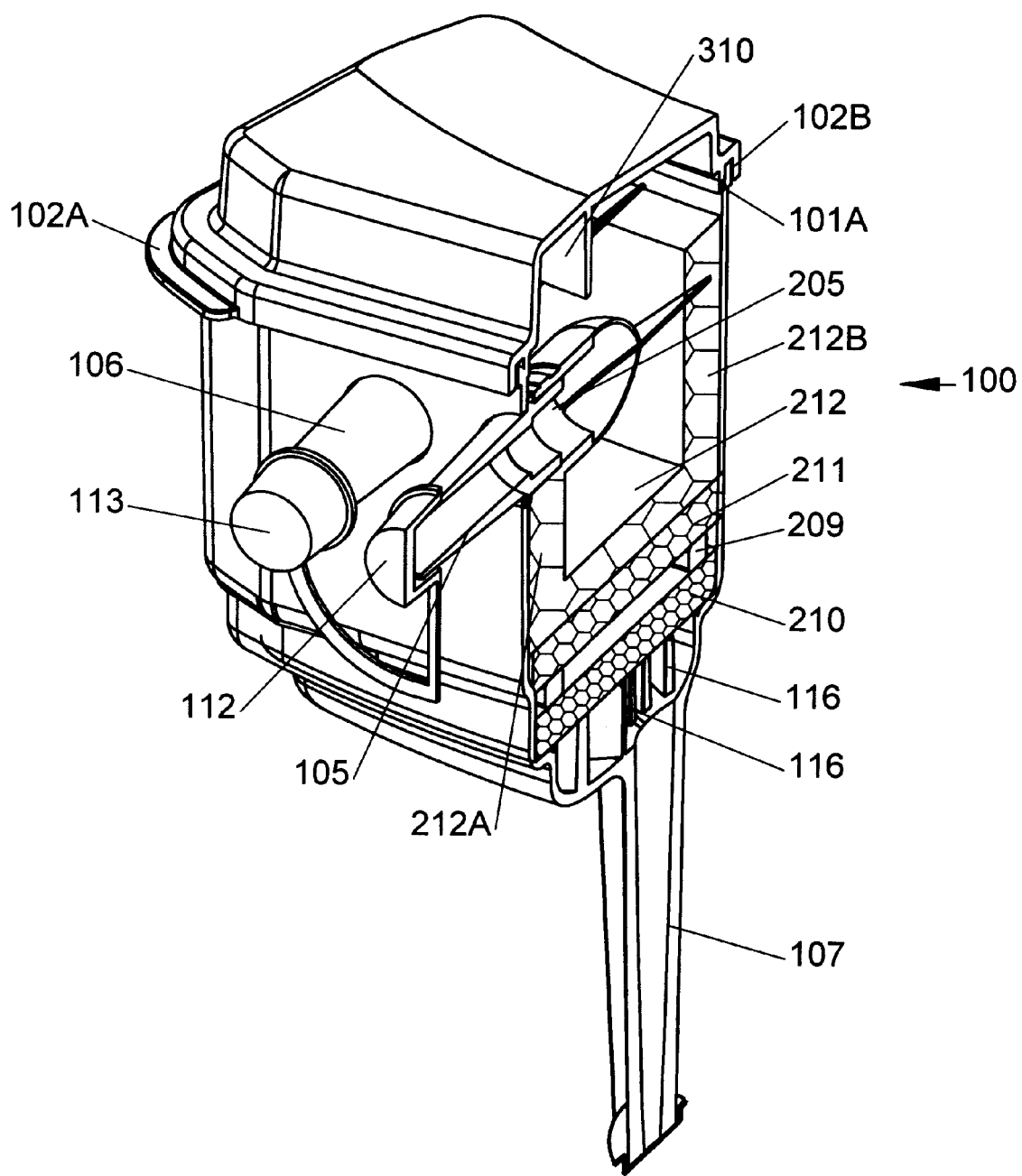
FIG. 4 is a partially broken away side or oblique view of the filtration system shown in FIG. 3.

Referring now to FIG. 4, there is shown a cut away view of the filtration system 100. The system includes the housing 101, lid 102 and outlet portal 107. Also, the inlet port 106 is shown complete while inlet port 105 is partially broken away. The port cap 113 is shown along with the partially broken away port cap 112 together with the optional leash 109 and leash ring 108.

A partially cutaway view of check valve 205 is shown inside the housing 101 and connected to port 105. The check valve is described infra.

Again, the ribs 116 (seen best in FIG. 5) are formed at the lower internal surface of housing 101 extending toward the opening in outlet port 107. The filter element 210 rests upon the interior ledge 118 adjacent the bottom of the housing 101 and, in some cases, upon the upper edges of ribs 116. The gasket 209 maintains the filter element in place as described supra. The filter element 211 is supported by gasket 209.

As seen in FIG. 4, the filter elements 212 rests on the filter elements 211. The filter element 212 includes the side wall portions 212A and 212B which are joined to the bottom section of the filter element 212. As noted supra, filter element 212 comprises a sofa-shaped, basket-like filter element which receives and filters all of the effluent from the check valves 203–206 before the flow passes through the other filter elements and out through outlet port 107. The decreasing porosity of the filter elements removes smaller sized, fluid borne matter as the fluid passes through the filter system.

Figure 5:
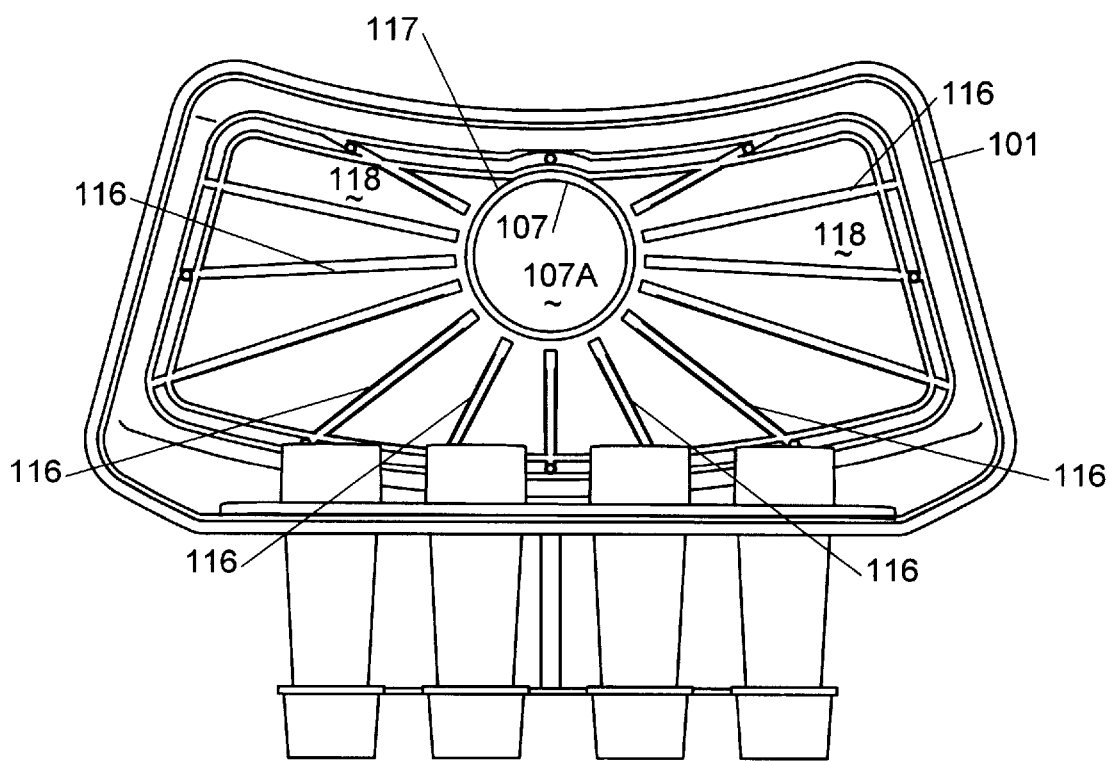
FIG. 5 is a top view of the housing for the filtration system shown in FIG. 1 with the lid and the internal components removed.

Referring now to FIG. 5, there is shown a top view of the housing 101 with the lid 102 and the several filter elements removed. In this view, the inlet ports 103–106 are shown formed integrally with the housing 101 and with the check valves removed. The bottom of the housing 101 is shown to incorporate a plurality of ribs 116 which extend generally radially from the opening 107A of outlet port 107 to the inner surface of the housing 101. The ribs 116 serve to channel the effluent which has passed through the filter elements into the opening 107A in outlet port 107. The rim 117 adjacent to opening 107A may be formed in the interior bottom surface 18 of the housing 101 and is sloped downwardly to enhance outward flow from housing 101 to the port 107. The inner, bottom, surface 118 of housing 101 may also be configured to slope from the perimeter thereof toward the outlet port 107 in order to enhance outward flow of effluent.

Figure 6:
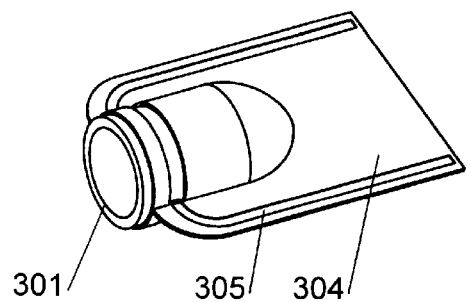
FIG. 6 is an oblique view of a check value shown in FIG. 2 and used in the filtration system of the instant invention.
Figure 7:
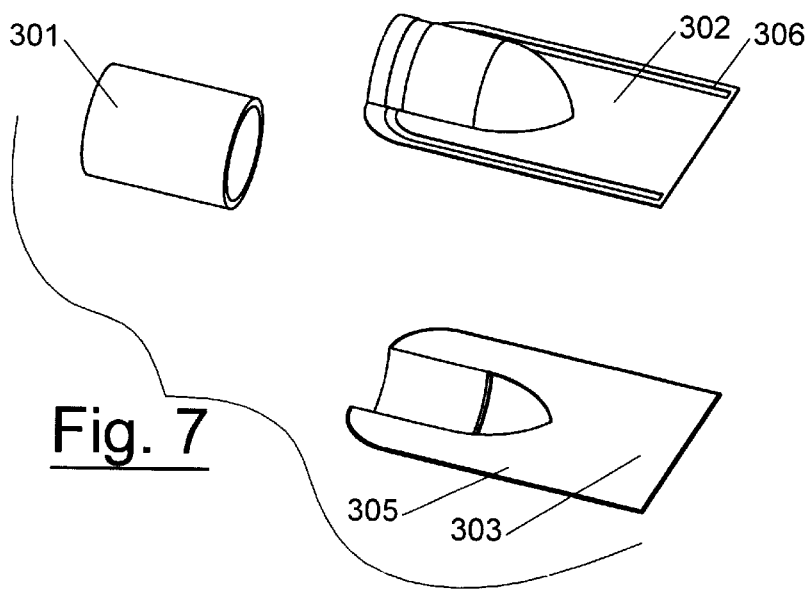
FIG. 7 is an exploded view of the check valve shown in FIG. 6.

Referring now concurrently to FIGS. 6 and 7, there are shown an assembled view and an exploded view, respectively, of the check valve 203, for example. The check valve 203 comprises a connector tube 301 which is designed to engage with the respective inlet port. Typically, the tube 301 is a short cylindrical tube which is relatively rigid in order to maintain its shape. However, the tube is able to snugly engage the inlet port and form a secure, leakproof connection therewith.

The check valve 203 also includes an elongated, flattened tube 304 which is, in this embodiment, formed by flaps 302 and 303 of generally planar, flexible material such as PVC. Flaps 302 and 303 each have one end joined to the connector tube 301 in suitable fashion, as for example by adhesives, RF bonding, sonic welding or the like to form a secure seal. The side edges of the flaps 302 and 303 are also sealed to each other in a suitable fashion as suggested above. Thus, the common end of the flaps 302 and 303 along with tube 301 forms a generally cylindrical opening which communicates with the space between the flaps which are sealed together at the side edges at seams 305 and 306 to form the flattened tube 304. The other ends of the flaps 302 and 303 are not sealed together but are independently flexible.

Figure 8A:
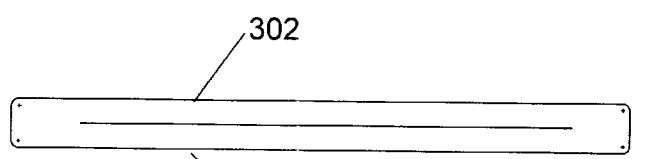
FIGS. 8A and 8B show the distal end of the check valve shown in FIG. 6 with the closed and open positions, respectively.

Thus, as shown in FIG. 8A, by properly selecting the dimensions of the components, the unsealed ends of the flaps 302 and 303 tend to come together snugly and form a closed end to the check valve.

Figure 8B:
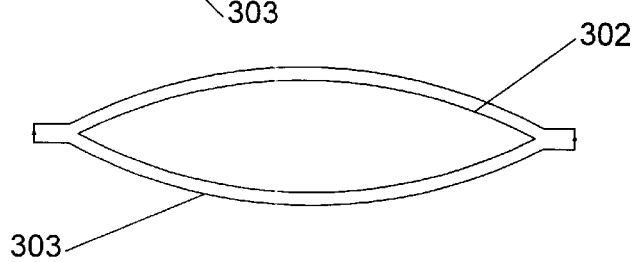

Conversely, as shown in FIG. 8B, the unattached ends of the flaps 302 and 303 can be spread apart by application of a modest force applied thereto by fluid passing through the check valve.

Thus, fluid can flow through the tube 301, through the channel in tube 304 defined between the edge-sealed flaps 302 and 303, and out the unsealed end of the check valve. However, inasmuch as the free ends of the flaps 302 and 303 tend to come together in the absence of a pressurized flow through the valve unidirectional flow is achieved and reverse flow through the check valve cannot occur.

It should he understood that the pressurized flow can be provided by supplying a positive pressure at the input side of connector tube 301 (e.g. via inlet ports 103–106) or by supplying a negative pressure (e.g. vacuum) at the unsealed end of the flaps at the distal end of the valve (e.g. via outlet port 107). In either case, unidirectional flow through the check valve is achieved.

Thus, there is shown and described a unique design and concept of a waste filter and manifold system. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

What is claimed is:

1. A filtration unit comprising, a substantially rigid housing, a plurality of inlet ports mounted at said housing, at least one outlet port mounted at said housing and spaced apart from said plurality of inlet ports, a plurality of check valves, each adapted to be attached to a respective one of said inlet ports and interposed between said inlet ports and said outlet port to control material flow therebetween in said housing, and a filter device interposed between said check valves attached to said inlet ports and said outlet port in said housing to filter the material flow therebetween.

2. The unit recited in claim 1 wherein, said filter device includes a plurality of filter components.

3. The unit recited in claim 2 wherein, each of said filter components exhibits a different filtration parameter.

4. The unit recited in claim 3 wherein, the filtration parameters of said components are from 5 to 100 pores per linear inch.

5. The unit recited in claim 3 wherein, said distal end includes a pair of flaps joined together at the sides thereof.

6. The unit recited in claim 1 wherein, each said inlet port is integrally formed with said housing.

7. The unit recited in claim 1 wherein, each inlet port is disposed at a side surface of said housing.

8. The unit recited in claim 1 wherein, said outlet port is disposed at a bottom surface of said housing.

9. The unit recited in claim 1 including, a cap for selectively covering each said inlet port.

10. The unit recited in claim 9 including, a connecting strap joined to each said cap.

11. The unit recited in claim 10 wherein, each said connection strap is selectively mounted to said outlet port.

12. The unit recited in claim 1 wherein, each said inlet port is mounted on a respective support which is affixed to said housing.

13. The unit recited in claim 12 wherein, said housing has a plurality of inlet port apertures therein, each for receiving a respective one of said inlet ports such that each said support is disposed within said housing.

14. The unit recited in claim 1 wherein, each said check valve is attached to an inlet port to permit only unidirectional flow through said housing.

15. The unit recited in claim 1 including, a filter support disposed within said housing and adapted to support said filter device thereon.

16. The unit recited in claim 1 including, at least one rib formed on an internal surface of said housing to direct material flow toward said outlet port.

17. The unit recited in claim 1 wherein, each said check valve includes a proximal end which is securely joined to a respective one of said inlet ports and a distal end which is selectively opened or closed to passage of material flow through said check valve from said inlet port.

18. The unit recited in claim 1 wherein, said filter device has portions thereof which exhibit different filtration parameters.

19. The unit recited in claim 1 wherein, said filter device is fabricated of reticulated polyurethane foam.

20. The unit recited in claim 1 wherein, each said check valve includes a proximal end and a distal end remote from said proximal end, said proximal end is normally open and is adapted to be joined to an inlet source, and said distal end includes at least one flexible portion which is adapted to flex to thereby permit material flow through said proximal end in one direction only.

\* \* \* \* \*